United States Patent
Baileys

(10) Patent No.: US 9,638,654 B2
(45) Date of Patent: May 2, 2017

(54) METHOD AND SYSTEM FOR HEALTH MONITORING OF COMPOSITE ELASTOMERIC FLEXIBLE ELEMENTS

(71) Applicant: Oil States Industries, Inc., Arlington, TX (US)

(72) Inventor: John Baileys, Arlington, TX (US)

(73) Assignee: OIL STATES INDUSTRIES, INC., Arlington, TX (US)

( * ) Notice: Subject to any disclaimer, the term of this patent is extended or adjusted under 35 U.S.C. 154(b) by 324 days.

(21) Appl. No.: 14/538,866

(22) Filed: Nov. 12, 2014

(65) Prior Publication Data

US 2015/0145533 A1 May 28, 2015

Related U.S. Application Data

(60) Provisional application No. 61/908,630, filed on Nov. 25, 2013.

(51) Int. Cl.
*G01R 27/26* (2006.01)
*G01N 27/24* (2006.01)
(Continued)

(52) U.S. Cl.
CPC .......... *G01N 27/24* (2013.01); *F16J 15/3296* (2013.01); *G01N 27/02* (2013.01);
(Continued)

(58) Field of Classification Search
CPC ........ G01N 27/02; G01N 27/22; G01N 27/24; G01N 33/44; G01R 27/26; G01R 27/2605;
(Continued)

(56) References Cited

U.S. PATENT DOCUMENTS 4,407,054 A 10/1983 Zipfel, Jr.
4,992,778 A 2/1991 McKeen et al.
(Continued)

FOREIGN PATENT DOCUMENTS

JP 2001033402 A 2/2001

OTHER PUBLICATIONS

Joyce, David, International Search Report and Written Opinion of the International Search Authority, International Application No. PCT/US2014/065257, Feb. 4, 2015, 10 pages, European Patent Office, Rijawijk, The Netherlands.
(Continued)

*Primary Examiner* — Hoai-An D Nguyen
(74) *Attorney, Agent, or Firm* — Polsinelli PC

(57) ABSTRACT

A composite elastomeric flexible element has an elastomer layer between rigid members. When subjected to loads, and as time goes by, the elastomer layer will undergo damage in the form of micro-voids and polymer chain scission. The time it takes the damage to reach a predetermined, but safe state is a known function of several parameters such as loading rate and load magnitude, time at load, temperature and frequency. The damage decreases the electrical permittivity of the elastomer and changes the electrical conductance of the elastomer if the elastomer is in the environment of an electrically conductive fluid or when the elastomer includes conductive filler. The health of the flexible element is monitored by measuring the electrical impedance of the elastomer layer, computing an indication of health from the electrical impedance and trend data for the elastomer layer, and reporting the indication of health to a human administrator.

22 Claims, 11 Drawing Sheets

(51) Int. Cl.
*G06F 3/041* (2006.01)
*G01N 27/02* (2006.01)
*G01N 33/44* (2006.01)
*F16J 15/3296* (2016.01)
*G06K 9/00* (2006.01)
*G01N 27/22* (2006.01)

(52) U.S. Cl.
CPC ......... *G01N 33/44* (2013.01); *G01R 27/2605* (2013.01); *G06F 3/0414* (2013.01); *G01N 27/22* (2013.01); *G01R 27/26* (2013.01); *G06K 9/0002* (2013.01)

(58) Field of Classification Search
CPC ........ G01D 5/24; G01D 5/2405; G01D 5/241; G01D 5/2412; G01D 5/2417; G06K 9/0002; G06F 3/0414; F16J 15/3296; H03K 17/955
USPC ....... 324/600, 649, 658, 661, 662, 663, 671, 324/686, 691, 519, 548, 76.11, 750.17; 702/47, 52
See application file for complete search history.

(56) References Cited

U.S. PATENT DOCUMENTS

| | | | |
|---|---|---|---|
| 5,034,848 A | 7/1991 | Rowlette et al. | |
| 5,311,140 A | 5/1994 | Permuy | |
| 5,325,869 A | 7/1994 | Stokes | |
| 5,392,658 A | 2/1995 | Okada | |
| 5,786,997 A | 7/1998 | Hoyt et al. | |
| 5,869,751 A | 2/1999 | Bonin | |
| 5,905,212 A | 5/1999 | Moses et al. | |
| 5,964,720 A | 10/1999 | Pelz | |
| 6,026,694 A | 2/2000 | Gray | |
| 6,105,438 A | 8/2000 | Gieseke | |
| 6,295,878 B1 | 10/2001 | Berme | |
| 6,329,812 B1 | 12/2001 | Sundin | |
| 6,354,155 B1 | 3/2002 | Berme | |
| 6,575,041 B2 | 6/2003 | Schwarz et al. | |
| 6,792,815 B2 | 9/2004 | McDearmon et al. | |
| 6,951,143 B1 | 10/2005 | Adderton et al. | |
| 7,024,295 B2 | 4/2006 | Oestreicher et al. | |
| 7,024,947 B2 | 4/2006 | Ishiguro et al. | |
| 7,117,119 B2 | 10/2006 | Van Dyk et al. | |
| 7,133,727 B2 | 11/2006 | Van Dyk et al. | |
| 7,237,444 B2 | 7/2007 | Berdichevsky et al. | |
| 7,320,253 B2 | 1/2008 | Hanazawa et al. | |
| 7,343,814 B2 | 3/2008 | Harish et al. | |
| 7,437,954 B2 | 10/2008 | Sakano | |
| 7,451,658 B2 | 11/2008 | Sills et al. | |
| 7,454,979 B2 | 11/2008 | Frank et al. | |
| 7,472,611 B2 | 1/2009 | Hanazawa et al. | |
| 7,493,827 B2 | 2/2009 | Madden et al. | |
| 7,500,406 B2 | 3/2009 | Morimoto | |
| 7,603,917 B2 | 10/2009 | Graham et al. | |
| 7,631,697 B2 | 12/2009 | Bhavsar | |
| 7,656,168 B2 | 2/2010 | Mahowald et al. | |
| 7,665,371 B2 | 2/2010 | Mastinu et al. | |
| 7,710,126 B2 | 5/2010 | Morimoto | |
| 7,712,366 B2 | 5/2010 | Beyeler | |
| 7,726,205 B2 | 6/2010 | Meyer et al. | |
| 7,739,922 B2 | 6/2010 | Inamori | |
| 7,884,624 B2 | 2/2011 | Wang et al. | |
| 7,902,841 B2 | 3/2011 | Reime | |
| 7,977,952 B2 | 7/2011 | Krutz et al. | |
| 8,019,570 B2 | 9/2011 | Van Dyk et al. | |
| 8,096,196 B2 | 1/2012 | Eilersen | |
| 8,098,120 B2 | 1/2012 | Steeneken et al. | |
| 8,099,672 B2 | 1/2012 | Van Dyk et al. | |
| 8,141,437 B2 | 3/2012 | Amirouche et al. | |
| 8,156,823 B2 | 4/2012 | Kim et al. | |
| 8,189,300 B1 | 5/2012 | Bonin | |
| 8,249,831 B2 | 8/2012 | Vock et al. | |
| 8,322,415 B2 | 12/2012 | Loretz et al. | |
| 8,344,526 B2 | 1/2013 | Bhat et al. | |
| 8,345,513 B2 | 1/2013 | Huang | |
| 8,446,360 B2 | 5/2013 | Baskett et al. | |
| 8,527,214 B2 | 9/2013 | Horak | |
| 8,943,884 B2 | 2/2015 | Kumar | |
| 2007/0078695 A1 | 4/2007 | Zingelewicz | |
| 2009/0189616 A1 | 7/2009 | Krutz et al. | |
| 2010/0082375 A1 | 4/2010 | Vivalda | |
| 2012/0017674 A1 | 1/2012 | Kumar | |
| 2013/0234734 A1* | 9/2013 | Iida ........................ | G06F 3/044 324/661 |
| 2014/0015745 A1* | 1/2014 | Chae ........................ | G06F 3/03 345/156 |
| 2014/0054438 A1* | 2/2014 | Yun ........................ | G06F 1/1652 248/550 |

OTHER PUBLICATIONS

Programmable Automatic RCL Meter PM6304, Users' Manual, Nov. 1995, Rev. 2, 158 pages, Fluke Corporation, Everett, WA.
Elastomer Testing Solutions, 2010, 8 pages, MTS Systems Corporation, Eden Prairie, MN.
George et al., Dielectric properties of isotactic polypropylene/nitrile rubber blends: Effects of blend ratio, filler addition, and dynamic vulcanization, Journal of Applied Polymer Science, Jul. 11, 1999, pp. 255-270, vol. 73, No. 2, John Wiley & Sons, Inc., Hoboken, NJ.
George et al., Chapter 7, Dielectric properties: Effects of blend ratio, filler addition, and dynamic vulcanisation, 1999, pp. 179-206, Mahatma Ghandi University, Kottayam, India.
MC14016B Quad Analog Switch/ Quad Multiplexer, Data Sheet, Aug. 2000, 12 pages, On Semiconductor, Denver, Co.
MC14066B Quad Analog Switch/ Quad Multiplexer, Data Sheet, Mar. 2000, 12 pages, On Semiconductor, Denver, Co.
MC56F847XX, Data Sheet, Aug. 2012, 69 pages, Freescale Semiconductor, Inc., Tempe, AZ.
8-Bit PIC® Micontrollers, Data Sheet, Apr. 2006, 16 pages, Microchip Technology Inc., Chandler, AZ.
Agilent 4263B LCR Meter Operation Manual, Jun. 2009, 330 pages, Agilent Technologies, Englewood, CO.
Boonton 7200 Series Capacitance Meter, Data Sheet, 2010, 4 pages, Wireless Telecom Group Inc., Parsippany, NJ.
Gunasekaran, S. et al., Dielectric studies of some rubber materials at microwave frequencies, Indian Journal of Pure & Applied Physics, Oct. 2008, pp. 733-737, vol. 46, National Institute of Science Communication and Information Resources, New Delhi, India.
Santulli, C. et al., Influence of Content and Diameter of Fibres and Chemical Treatment on the Dielectric Properties of Oil Palm Fibres—Rubber Composites, Science and Engineering of Composite Materials, 2009, pp. 77-88, vol. 16 (2), Scientific & Academic Publishing, Rosemead, CA.
Evaluation of asset integrity management system (AIMS), 2012, 28 pages, Department of Mines and Petroleum, Government of Western Australia, East Perth, Australia.
Shahir, Syahriman MD, et al., SGS Best Approach in Asset Integrity Management Process: Case Study 1: SGS Experiences in Refining Facility, Sep. 2013, 21 pages, SGS Industrial Services, Karachi, Pakistan.
Potty, Narayanan Sambu, et al., Structural Integrity Management for Fixed Offshore Platforms in Malaysia, World Academy of Science, Engineering and Technology, 2009, pp. 1079-1087, vol. 34, World Academy of Science, Engineering and Technology Organization, Riverside, CT.
Usman, M.A. et al., An Innovative Approach to Managing the Integrity of Oil and Gas Pipelines: Pipeline Integrity Management System, Petroleum and Coal, 2012, pp. 1-8, vol. 54 (1), VURUP, a.s., Bratislava, Slovak Republic.
SCR Sizes, internet web page at oilstates.com, 2007, one page, Oil States Industries, Inc, Arlington, TX.
SCR Features, Internet web page at oilstates.com, 2007, one page, Oil States Industries, Inc, Arlington, Tx.
Tendon Systems, Internet web page at oilstates.com, 2007, one page, Oil States Industries, Inc. Arlington, Tx.

(56) References Cited

OTHER PUBLICATIONS

FlexJoint Tendon Bearing, Internet web page at oilstates.com, 2007, one page, Oil States Industries, Inc. Arlington, Tx.

* cited by examiner

METHOD AND SYSTEM FOR HEALTH MONITORING OF COMPOSITE ELASTOMERIC FLEXIBLE ELEMENTS

RELATED APPLICATIONS

The present application claims the benefit of John Baileys, U.S. Provisional Application Ser. No. 61/908,630 filed Nov. 25, 2013 entitled "Method and System for Health Monitoring of Composite Elastomeric Flexible Elements," incorporated herein by reference.

FIELD OF THE INVENTION

The present invention relates generally to composite elastomeric flexible elements of the kind having elastomer layered between rigid members. The present invention relates specifically to a method and system for monitoring the health of the elastomer in such a composite elastomeric flexible element by measurement of electrical impedance of the elastomer.

BACKGROUND OF THE INVENTION

Composite elastomeric flexible elements are commonly used between load-bearing structural members in order to accommodate motion between the structural members while significantly reducing mechanical fatigue of the structural members and providing some resistance to the motion. For example, composite elastomeric flexible elements are used for supporting structural members of buildings, bridges, and floating offshore drilling and production facilities, in order to accommodate motion due to a variety of sources. These sources range from frequent recurring events to infrequent extreme events. For example, a building or bridge may accommodate recurring thermal expansion and contraction due to daily and seasonal variation in temperature, as well as infrequent extreme events such as wind loading due to violent storms and seismic shock due to earthquakes. Floating offshore drilling and production facilities may accommodate recurring wave and tidal motion, as well as infrequent extreme events such as violent storms and collisions with other vessels.

Recently there has been a desire to monitor the health of structural members in order to maintain structural integrity while controlling maintenance costs by more intelligent scheduling of repair and replacement of the structural members. For example, there has been an increased public awareness of aging infrastructure due to news reports of collapsing bridges and leaking pipelines. There has been a corresponding interest among several oil companies in "asset integrity management" of their infrastructure. Integrity management encompasses a broad scope of threats, from corrosion and stress fatigue, to "third party" damage such as sabotage. The focus has been on the stresses and strains developed in metal parts, and such methods have involved visual inspections as well as mechanical and electromechanical solutions.

SUMMARY OF THE INVENTION

A composite elastomeric flexible element has an elastomer layer between rigid members. When subjected to loads, and as time goes by, the elastomer layer will undergo damage in the form of micro-voids and polymer chain scission. For each elastomer pad, the time it takes the degradation in the elastomer layer to reach a pre-established, but still safe state of damage is a known function of several parameters such as geometry, load magnitude, loading rate, time at load, temperature and frequency. The degradation caused by damage decreases the electrical permittivity of the elastomer, and decreases the electrical conductance of the elastomer when the elastomer includes conductive filler. The health of the composite elastomeric flexible element is monitored by measuring the electrical impedance of the elastomer layer, computing an indication of health of the composite elastomeric flexible element from the measured electrical impedance of the elastomer layer and trend data for the elastomer layer, and reporting the indication of health to a human administrator. For example, the trend data for the elastomer layer shows degradation of the elastomer layer over time under load, and the indication of health of the composite elastomeric flexible element includes an estimate of the remaining time until the elastomer layer would reach a pre-established state of damage under load. In any case, measurement of the electrical impedance of the elastomer layer provides a practical way of monitoring the health of the composite elastomeric flexible element. Moreover, a decrease in electrical permittivity and electrical conductance can be detected before the elastomer reaches the pre-established state of damage. In either case, electrical impedance of the elastomer layer provides an indication of health of the composite elastomeric flexible element.

In accordance with one aspect, the invention provides a method of monitoring health of a composite elastomeric flexible element having an elastomer layer between rigid members. The method includes measuring electrical impedance of the elastomer layer, computing an indication of health of the composite elastomeric flexible element from the measured electrical impedance of the elastomer layer and trend data for the elastomer layer, and reporting the indication of health of the composite elastomeric flexible element to a human administrator.

In accordance with another aspect, the invention provides a system for monitoring health of a composite elastomeric flexible element having an elastomer layer between rigid members. The system includes a circuit for measuring electrical impedance of the elastomer layer. The system also includes a data processor coupled to the circuit for receiving a measurement of electrical impedance of the elastomer layer, and executing computer program instructions stored in memory to perform the steps of computing an indication of health of the composite elastomeric flexible element from the measured electrical impedance of the elastomer layer and trend data for the elastomer layer, and reporting the indication of health of the composite elastomeric flexible element to a human administrator.

BRIEF DESCRIPTION OF THE DRAWINGS

Additional features and advantages of the invention will be described below with reference to the drawings, in which.

Figure 1:
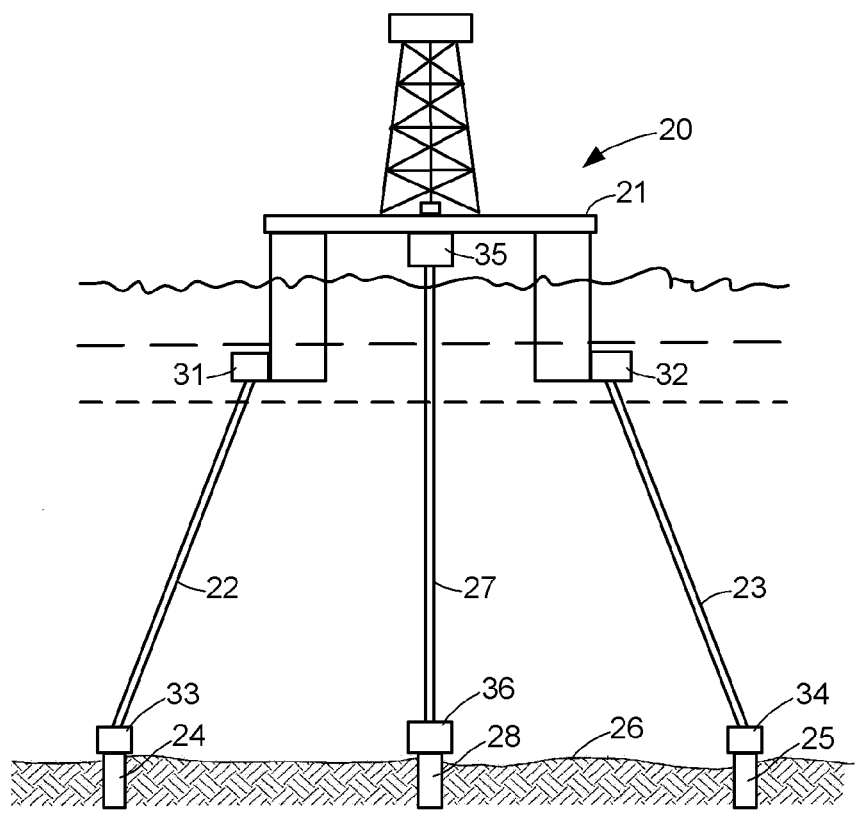
FIG. 1 is a schematic diagram of a floating offshore drilling and production facility.

While the invention is susceptible to various modifications and alternative forms, specific embodiments thereof have been shown in the drawings and will be described in detail. It should be understood, however, that it is not intended to limit the invention to the particular form shown, but on the contrary, the intention is to cover all modifications, equivalents, and alternatives falling within the scope of the invention as defined by the appended claims.

DETAILED DESCRIPTION OF THE PREFERRED EMBODIMENTS

With reference to FIG. 1, there is shown a floating offshore drilling and production facility 20 having a floating tension leg platform 21 (TLP). The TLP 21 is stabilized by tubular steel tendons 22, 23 coupling the TLP to anchors or piles 24, 25 in the seabed 26. A drilling or production riser 27 descends from the TLP 21 to a well head or casing 28 in the seabed 26. The drilling or production riser 27 provides a conduit for a drill string or downhole tools for drilling, well logging, and well maintenance operations. The drilling or production riser 27 also provides a conduit for the flow of drilling fluid or production fluid between the TLP 21 and the well head 28.

The floating offshore drilling and production facility 20 is subject to the natural effects of wind, waves, and current, resulting in movement of the structure. The facility 20 has multiple composite elastomeric flexible elements for accommodating this movement while significantly reducing mechanical fatigue of the structural components such as the tendons 22, 23 and the riser 27. A respective composite elastomeric flexible element 31, 32 couples each of the tendons 22, 23 to the TLP 21. A respective composite elastomeric flexible element 33, 34 also couples each of the tendons 22, 23 to an anchor or pile 24, 25 on the seabed 26. A flexible pipe joint 35 is mounted to the TLP 21 and is attached to the top of the riser 27. A flexible pipe joint 36 is mounted to the wellhead 28 and is attached to the bottom of the riser 27. Each of the flexible pipe joints 35, 36 includes a respective composite elastomeric flexible element.

Figure 2:
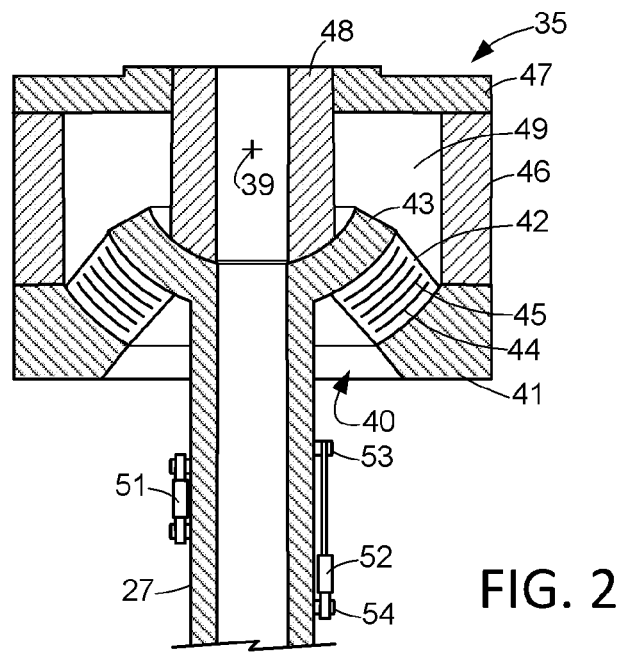
FIG. 2 is a schematic diagram of a flexible pipe joint used to support a riser of the floating offshore drilling and production facility of FIG. 1.

FIG. 2 shows a lateral cross-section of the flexible pipe joint 35. The flexible pipe joint 35 includes a composite elastomeric flexible element 40. The composite elastomeric flexible element 40 includes a load ring 41, elastomer 42 supported on the load ring 41, and an upper flange 43 supported on the elastomer 42. The upper flange 43 is attached to the top of the riser 27, so that the load ring 44 supports the weight of the riser 27. The composite elastomeric flexible element 40 is annular so that the riser 27 passes though the composite elastomeric flexible element 40. Multiple rigid reinforcements 44, 45 are embedded in the elastomer 42. The upper flange 43 and the reinforcements 44, 45 are semi-spherical about a common center point 39 to facilitate pivoting of the riser 27 about the center point 39. The elastomer 42 provides some resistance to and dampening of the pivoting of the riser 27.

The flexible pipe joint 35 further includes a cylindrical housing 46 secured to the load ring 41, a cover 47 secured to the housing 46, and an inner pipe 48 descending from the cover 47 and providing a conduit to the riser 27. The housing 46 and cover 47 enclose an inner annular region 49 that becomes filled with drilling fluid or production fluid when the drilling fluid or production fluid flows through the riser 27. The composite elastomeric flexible element 40 provides a seal to contain the drilling fluid or production fluid so that the drilling fluid or production fluid is not released into the sub sea environment.

For measurement of stresses and strains developed in the riser 27 and in the flexible pipe joint 35, an inclinometer 51 and a tension sensor 52 are mounted to the riser 27. The tension sensor 52 measures elongation of the riser 27 over a distance between two attachment points 53 and 54. Such a tension sensor may use an inductive displacement sensor to measure the elongation; for example, as described in Madden et al. U.S. Pat. No. 7,493,827 issued Feb. 24, 2009.

Like any other structural component, the layers of the elastomer 42 in the flexible pipe joint 35 are subject to damage under load. The most extreme manifestation of this damage results in partial extrusion of the elastomer from between the rigid reinforcements 44, 45, which are intended to contain it. Although such a mode of failure does not result in a catastrophic event, it decreases rotational, axial and sideways stiffness so that the flexible pipe joint 35 no longer provides the resistance and dampening of motion for which it was originally designed to accommodate. Further damage, however, may result in a failure of the flexible pipe joint 35 to contain fluid within the riser 27, which may result in costly environmental pollution. Therefore there is a desire for a way to monitor the mechanical health of the flexible pipe joints 35, 36 and the other composite elastomeric flexible elements 31, 32, 33, and 34 in the facility 20 of FIG. 1.

The inventor has discovered a way of detecting degradation of the elastomer 42 before the elastomer 42 becomes extruded from the reinforcements 44, 45 and before this degradation becomes excessive. As will be described below, this degradation of the elastomer 42 can be detected by measuring electrical impedance of the elastomer 42. Before the elastomer 42 becomes extruded from the reinforcements 44, 45, this degradation may significantly impair the ability of the elastomer 42 to resist shear deformation and dampen loads and provide a fluid seal in a flexible pipe joint 35.

Figure 3:
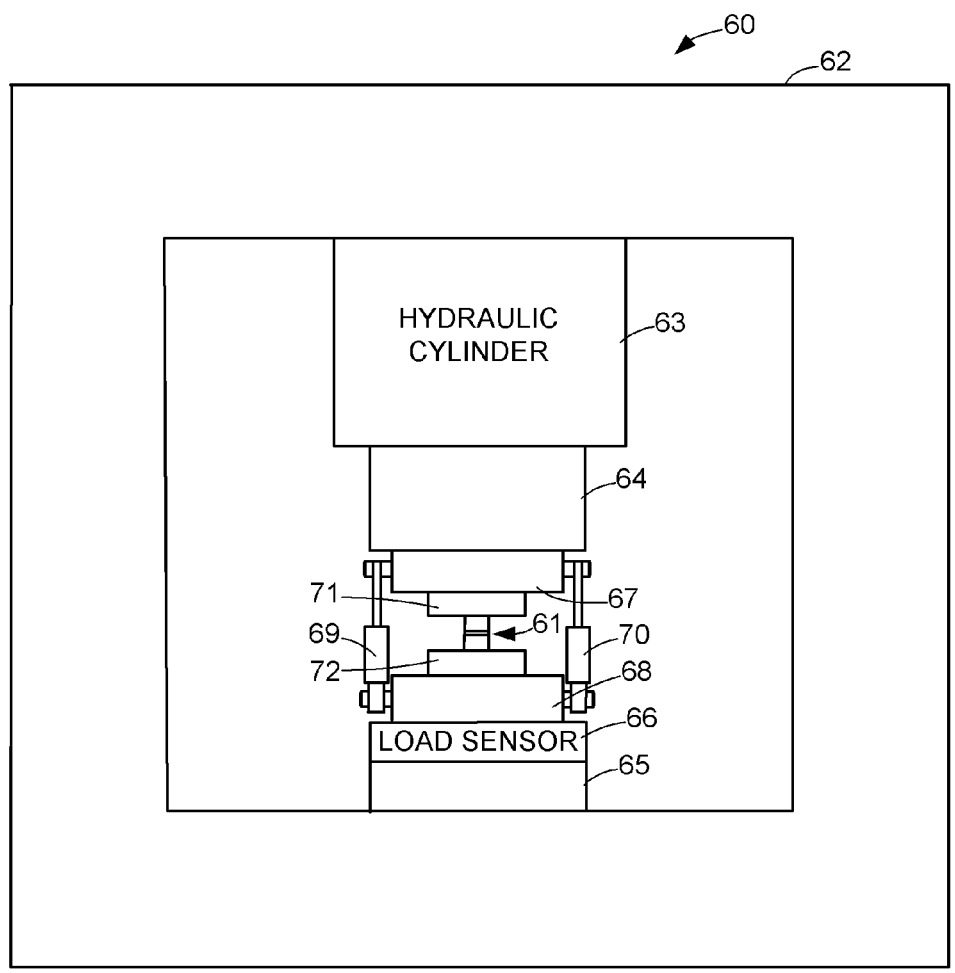
FIG. 3 is a schematic diagram of a test facility for applying a load to a composite elastomeric flexible element and measuring displacement of the composite elastomeric flexible element in response to the applied load.

FIG. 3 shows a test facility 60 for applying a compressive load to an elastomeric flexible element 61 and measuring displacement of the elastomeric flexible element 61 in response to the applied load. The test facility 60 is a kind of hydraulic press having a frame 62 and a hydraulic cylinder 63 and piston 64 for compressing an assembly inserted between the piston 64 and an anvil 65 mounted to the bottom of the frame 62. In this example, a load sensor 66 is placed on the anvil 65, and a pair of steel blocks 67, 68 coupled by two linear voltage displacement transducers (LVDT) 69, 70 are mounted between the steel blocks 67, 68. The elastomeric flexible element 61 and two rigid fiberglass sheets 71, 72 are place between the steel blocks 67, 68.

Figure 4:
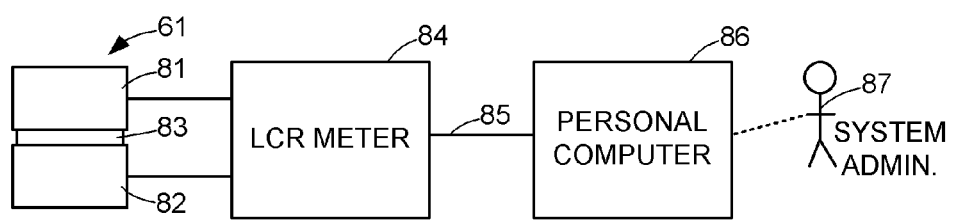
FIG. 4 is a schematic diagram of a system for measuring electrical impedance of an elastomer layer in the composite elastomeric flexible element in FIG. 3 in response to the applied load.

As further shown in FIG. 4, the elastomeric flexible element 61 includes two steel cylinders 81, 82 separated by a circular disk 83 of elastomer, such as nitrile butadiene rubber (NBR) reinforced with carbon black. The steel cylinders 81, 82 are connected to an inductance-capacitance-resistance (LCR) meter 84 to measure the electrical impedance between the two steel cylinders 81, 82. The LCR meter 84 is connected by a USB cable 85 to a personal computer 86 to continuously record the capacitance and resistance measured by the LCR meter 84 as the hydraulic cylinder (63 in FIG. 3) applies a monotonically increasing compressive load to the elastomeric flexible element 61. The personal computer 86 is also connected to the two linear voltage displacement transducers (LVDT 69, 70 in FIG. 3) of the frame (62 in FIG. 3) to continuously record the measured displacements as the hydraulic cylinder (63 in FIG. 3) applies a monotonically increasing compressive load to the elastomeric flexible element 61.

Figure 5:
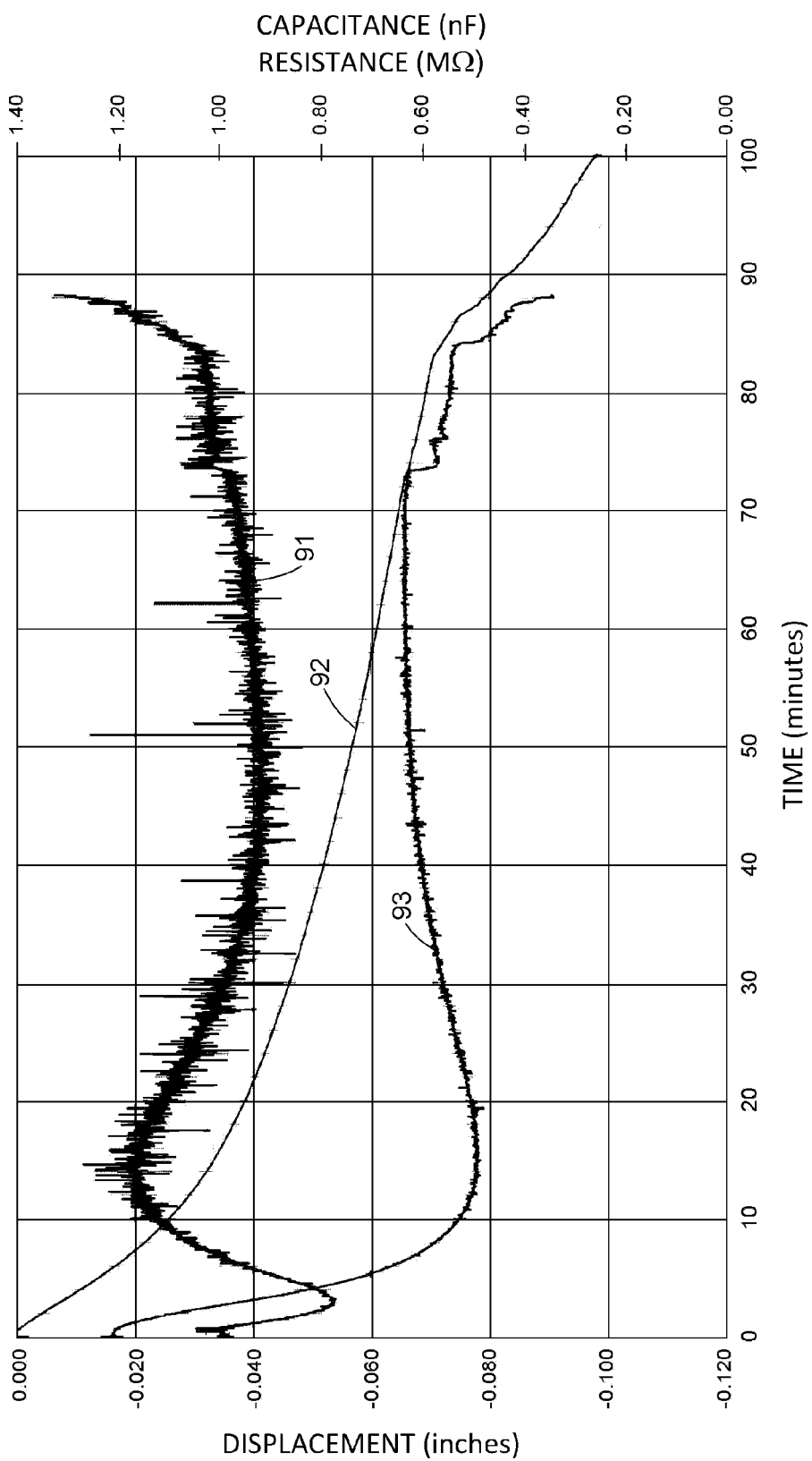
FIG. 5 is a graph of the displacement and capacitance and resistance of the elastomer layer in the composite elastomeric flexible element in FIG. 3 as a function of time as the composite elastomeric flexible element is subjected to a monotonic compressive load.

In a specific example, the elastomer was NBR, and the elastomeric flexible element 61 had a diameter of 1.6 inches (4.06 cm) and an initial elastomer thickness of about 70 mills (0.178 cm). The test facility used a MTS servo-hydraulic load frame having a 110-kip (489 kilo-Newton) capacity. The load frame applied a monotonic compressive load at a rate of 500 pounds of force (2224 Newtons) per minute until failure of the elastomer was achieved. The load frame was in an environmental chamber held at 120° F. (48.8° C.). Capacitance and resistance measurements were taken with a Fluke PM6304 Programmable Automatic LCR meter, using a test signal of 1 volt AC at 1.0 KHz. The results of this specific example are shown in FIG. 5. The top curve 91 is the measured resistance. The middle curve 92 is the arithmetic average of the displacement measurements from two LVDTs. The bottom curve 93 is the measured capacitance.

The test results are interpreted as follows. An event occurred at approximately 73 minutes into the test, as indicated by a non-linear change in both capacitance and displacement. This is symptomatic of the beginning of internal failure of the elastomer, as seen in historical compression endurance threshold testing. Then at approximately 84 minutes, rubber extruded from the test specimen, and a more pronounced change in capacitance and displacement is noted. Although the signal is less stable, the same events can be discerned from the resistance data.

Figure 6:
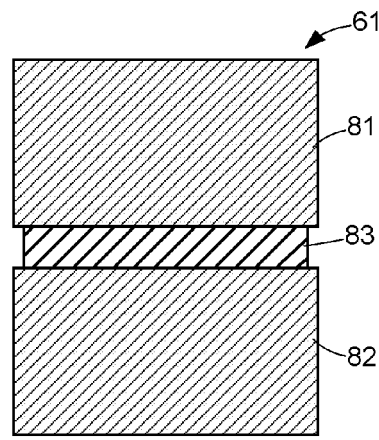
FIG. 6 is a cross-section of the composite elastomeric flexible element in the system of FIGS. 3 and 4 before the application of the compressive load.
Figure 7:
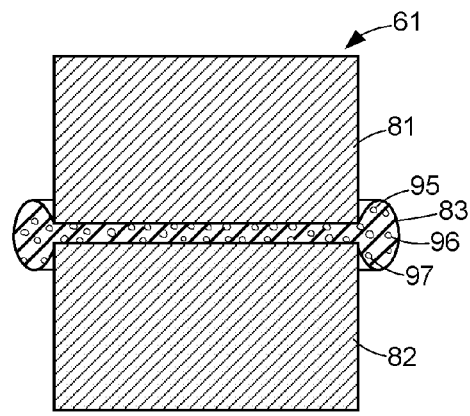
FIG. 7 is a cross-section of the composite elastomeric flexible element in the system of FIGS. 3 and 4 once the application of the compressive load has achieved failure of the elastomer.

FIG. 6 depicts the test specimen at the start of the test, and FIG. 7 depicts the test specimen at the end of the test, showing the extrusion of the rubber. A hypothesis explaining the non-linear change in both capacitance and resistance during the event at 73 minutes into the test is the formation of micro-voids, or polymer chain ruptures 95, 96, 97 in the elastomer. Also, the resistance signal continues to have increased fluctuations up to the time that extrusion was noticed, indicating creep of the elastomer with respect to the contacting surfaces of the steel cylinders 81, 82.

Most surprising is the relatively large magnitude of the change in capacitance and resistance during the event at 73 minutes into the test in comparison to the relatively small change in displacement during the event. A relatively large change in capacitance being caused by void formation and rubber creep is consistent with the published relative dielectric constant for NBR of about 21 at 1 KHz. (See FIG. 7.4, Variation of dielectric constant of PP/NBR blends with NBR content, in George et al., Dielectric properties of isotactic polypropylene/nitrile rubber blends: Effects of blend ratio, filler addition, and dynamic vulcanization, Journal of Applied Polymer Science, vol. 73, no. 2, pp. 255-270, 1999.) A relatively large change in resistance and resistance fluctuations caused by voids and rubber creep are consistent with the resistance being due to loss of contact pressure upon graphite particles of the carbon black filler by analogy to the operation of a carbon button microphone.

The relatively large change in capacitance and resistance during the event at 73 minutes into the test provides a practical way of detecting significant elastomer degradation that otherwise would not be detectable. Between the event at 73 minutes and the complete failure of the elastomer beginning at about 84 minutes, the elastomer is still capable of supporting a compressive load, yet the elastomer has become severely degraded for resisting and dampening shear loads, dampening compressive load variations, and for providing a perfect fluid seal. For asset integrity management, such degradation of the elastomer should be detected and reported to a systems administrator in order to schedule replacement of the composite elastomeric flexible element. It may also be possible to reduce the loading on the structure prior to replacement of the composite elastomeric flexible element in order to prevent further damage to the structure. In the case of a flexible pipe joint carrying production fluid under pressure, it may be possible to eliminate the fluid pressure by shutting off the flow of production fluid from the wellhead, in order to prevent a leak of the production fluid through the degraded elastomer and into the surrounding environment.

Figure 8:
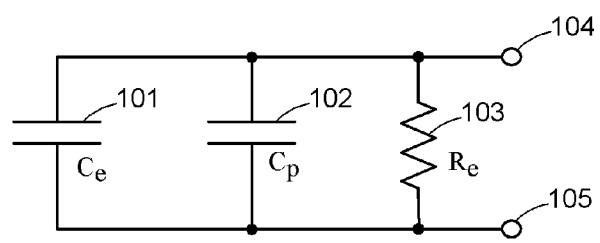
FIG. 8 is an electrical circuit model of the composite elastomeric flexible element in the system of FIGS. 3 and 4.

FIG. 8 shows an electrical circuit model of the composite elastomeric flexible element 61 used in the system of FIGS. 3 and 4. The electrical circuit model includes a parallel combination of a capacitor 101 representing the electrical capacitance ($C_e$) of the elastomer layer 83, a capacitor 102 representing parasitic capacitance ($C_p$) due to the electric field between the steel cylinders 81, 82 that is outside of the elastomer layer 83, and a resistor 103 representing the electrical resistance ($R_e$) of the elastomer layer. In accordance with this electrical circuit model and circuit theory, the electrical impedance $Z(\omega)$ at the terminals 104, 105 (representing respective electrical connection points to the steel cylinders 81, 82) is a function of angular frequency $\omega=2\pi f$ according to $Z(\omega)=R_e(C_e+C_p)/(j\omega R_e C_e+C_p)$, where "j" represents the square root of minus one. At zero frequency, the impedance $Z(0)=R_e$. At an angular frequency much greater than $1/(R_e(C_e+C_p))$, the impedance $Z(\omega)$ is approximately $(C_e+C_p)/j\omega$. The capacitance of the elastomer layer 83 is a function of the area (A) and thickness (d) of the elastomer layer 83 according to $C_e = \in_o \in_r A/d$, where $\in_o$ is the permittivity of free space, and $\in_r$ is the relative permittivity (i.e., the relative dielectric constant) of the elastomer. The resistance of the elastomer layer 83 is a function of the area (A) and thickness (d) of the elastomer layer 83 according to $R_e = \sigma_e A/d$, where $\sigma_e$ is the conductivity of the elastomer.

Figure 9:
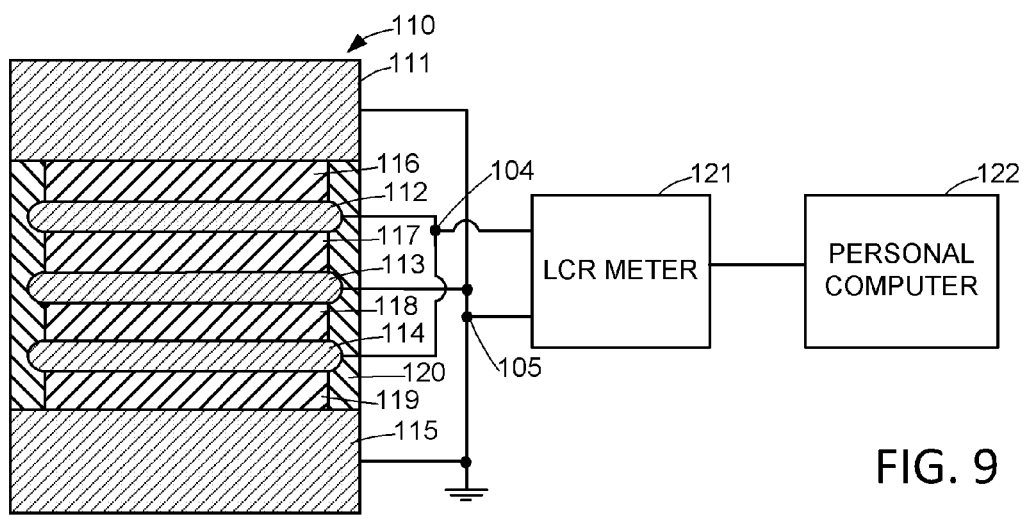
FIG. 9 shows a way of measuring electrical impedance of a composite elastomeric flexible element including a stack of electrically conductive rigid members and layers of elastomer between the rigid members.

FIG. 9 shows a way of measuring electrical impedance of a composite elastomeric flexible element 110 including a stack of multiple electrically conductive rigid members 111, 112, 113, 114, 115. The rigid members 111, 115 at the top and bottom of the stack are relatively thick and are used for applying a load to the composite elastomeric flexible element 110. The rigid members 112, 113, 114 inside the stack are relatively thin reinforcements. Each neighboring pair of rigid members is separated by a respective elastomer layer including a respective inner elastomer pad 116, 117, 118, 119. The rigid reinforcements 112, 113, 114 and the inner elastomer pads 116, 117, 118, 119 are enclosed in an outer layer of cover rubber 120. The outer layer of cover rubber 120 is relatively soft compared to the rubber pads 116, 117, 118, 119.

For example, in the case depicted in FIG. 9, in order to reduce the parasitic capacitance ($C_p$), the composite elastomeric flexible element 110 has an odd number of rigid members 111, 112, 113, 114, 115. The outer rigid members 111, 115 are connected in parallel to a ground potential, and alternate rigid members are connected in parallel. Thus, in FIG. 9, the rigid members 111, 113, 115 are connected in parallel to the grounded terminal 105, and the rigid members 112, 114 are connected in parallel to the other terminal 104. The terminals 104, 105 are connected to an LCR meter 121 for measuring the capacitance and resistance of the composite elastomeric flexible element 110 across the terminals 104, 105, and the LCR meter is linked to personal computer 122 for transmitting the capacitance and resistance measurements to the personal computer 122.

For example, the electrically conductive rigid members 111, 112, 113, 114, 115 are made of steel or other metal or composite material. Composite material is rendered conductive by incorporating conductive filler such as carbon fiber and carbon black into the composite material, or by applying conductive plating or coating to the surface of the composite rigid members. The rubber pads 116, 117, 118, 119 are molded separately, and then coated with bonding agent and stacked with the rigid members in a mold, and then the cover rubber is injection molded over the stack of rigid members and rubber pads, and the composite elastomeric flexible element 110 is cured under heat and pressure in the mold. Flexible wire leads may be attached to the reinforcements 112, 113, 114 either before or after the molding process. In either case, the flexible wire leads pass through the cover rubber 120 so that the wire leads are exposed to minimal stress and strain, and the wire leads do not cause stress or strain in the rubber pads 116, 117, 118, and 119. If the wire leads are attached to the reinforcements 112, 113, 114 after the molding process, for example by inserting the wire leads through holes drilled through the cover rubber 120 into the reinforcements 112, 113, 114, then the holes and electrical connections are sealed with a sealant such as rubber cement.

Because the cover rubber seals the reinforcements 112, 113, and 114 from the external environment, the capacitance and resistance measurements are relatively unaffected by the external environment so long as the cover rubber 120 remains intact. When the composite elastomeric flexible element 110 is in contact with an electrically conductive fluid, degradation of the elastomer may result in intrusion of the conductive fluid into the cover rubber 120 and into the rubber pads 116, 117, 118, 119. This will provide a conductive path between the rigid members and through the conductive fluid, which will cause the composite elastomeric flexible element to have a very low electrical resistance ($R_e$) between the terminals 104, 105. In the floating offshore facility 20 in FIG. 1, a very low electrical resistance of a composite elastomeric flexible element indicates intrusion of seawater, drilling fluid, or production fluid into the elastomer.

Figure 10:
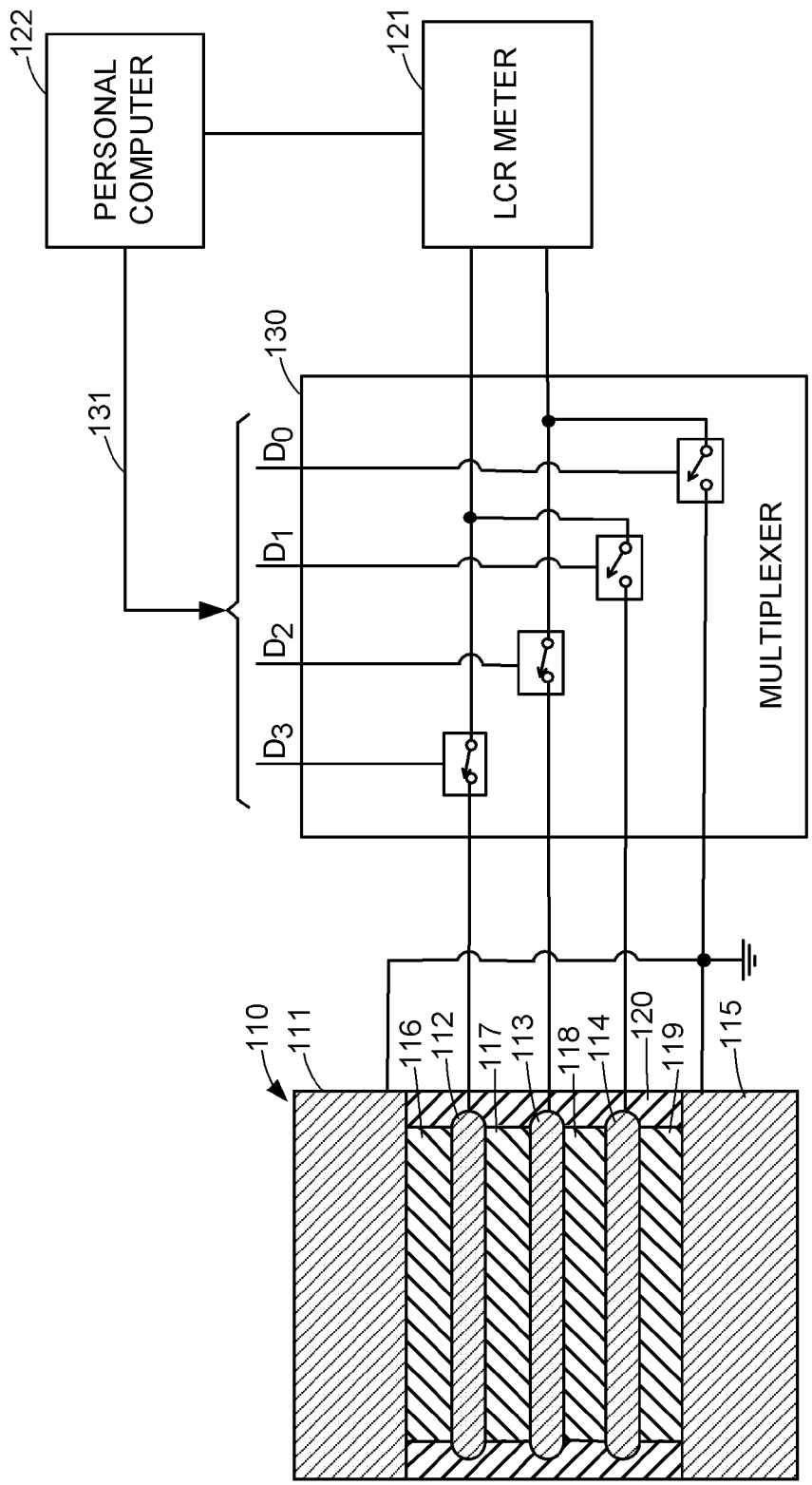
FIG. 10 shows the addition of a multiplexer to the system of FIG. 9 for obtaining a respective measurement of electrical impedance of each of the elastomer layers.

FIG. 10 shows the addition of a multiplexer 130 to the system of FIG. 9 in order to obtain a respective measurement of electrical impedance of each of the elastomer layers 116, 117, 118, 119. The multiplexer 130 is controlled by a nibble of information from a parallel output bus 131 of the personal computer 122. For example, the bus 131 is a Centronics IEEE-1284 parallel printer bus, and the multiplexer 130 is a complementary metal oxide semiconductor (CMOS) integrated circuit part No. 4016 or 4066. The value of a hexadecimal digit on the parallel output bus 131 selects the impedance to be measured. For example, a hexadecimal value of 9 selects the impedance of layer 116, a hexadecimal value of "C" selects the impedance of layer 117 (in the fashion shown in FIG. 10), a hexadecimal value of 6 selects the impedance of layer 118, a hexadecimal value of 3 selects the impedance of layer 119, and a hexadecimal value of "F" selects the impedance of all four of the layers in parallel to provide measured values of capacitance and resistance similar to that of the circuit in FIG. 9.

From the respective measurement of impedance of each of the elastomer layers, one obtains an indication of the dispersion, precision, and reliability of the measurements. For example, the relative change in impedance of each of the layers should be substantially similar absent elastomer degradation since the composite elastomeric flexible element is designed to have substantially the same levels of axial stress and strain in each of the elastomer layers. By calculating the variance of the relative change in impedance of the layers, one obtains a measure of variation that is relatively independent of stress and strain. Initially, when the elastomer is new and has not been exposed to excessive loads, the variance indicates the precision with which the system can measure the impedance. When the elastomer degrades, the variance will increase, since the degradation process will accelerate once it has begun, just as a chain is likely to fracture at its weakest link without fracturing the other links.

From the respective measurement of impedance of each of the elastomer layers, one may also identify and diagnose limitations and faults of the LCR meter and the lead wires connected to the rigid elements. For example, failure of a lead wire will most likely result in a minimum value of capacitance and a maximum value of resistance for a particular pair of elastomer layers that are adjacent to the same rigid reinforcement or are adjacent to the grounded rigid reinforcements 111, 115 at the ends of the stack. Also the sum of the capacitances of the individual layers should be substantially equal to the capacitance measured when the multiplexer electrically connects all of the layers in parallel, in accordance with the formula for the capacitance of capacitors connected in parallel. In this case the difference in capacitance indicates the precision with which the LCR meter is measuring the capacitance. In a similar fashion, the reciprocal of the sum of the reciprocals of the resistances of the individual layers should be substantially equal to the resistance measured when the multiplexer electrically connects all of the layers in parallel, in accordance with the formula for the resistance of resistors connected in parallel. In this case the difference in resistance indicates the precision with which the LCR meter is measuring resistance.

Figure 11:
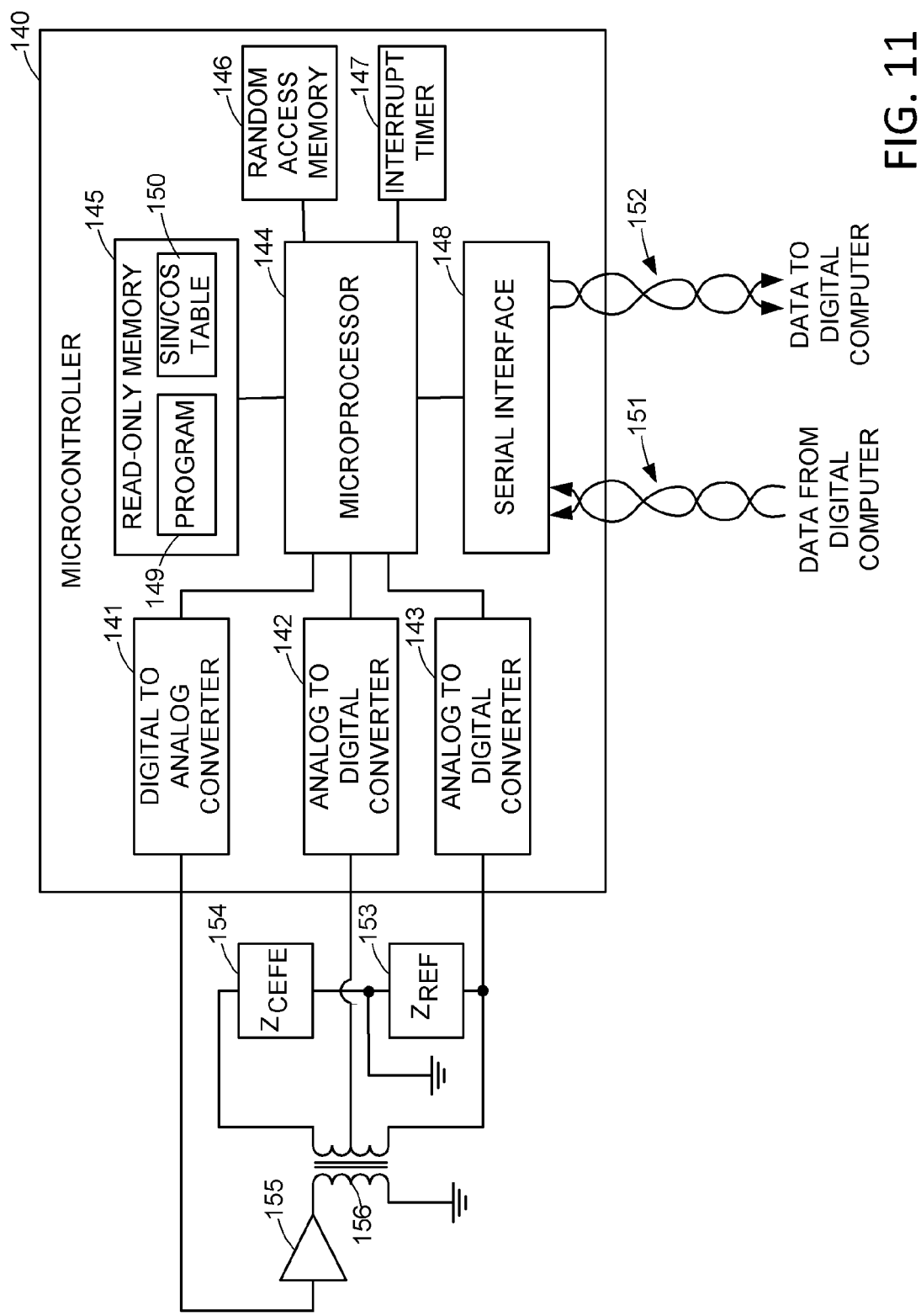
FIG. 11 is a schematic diagram of a circuit for configuring a microcontroller to function as a LCR meter for measuring electrical impedance of a composite elastomeric flexible element.

FIG. 11 shows a microcontroller 140 configured to function as a LCR meter for measuring the electrical impedance ($Z_{CEFE}$) of a composite elastomeric flexible element 154. In practice, it is desired to put a LCR meter at the location of each of the composite elastomeric flexible elements in a structure, and to transmit the capacitance and resistance measurements from the LCR meters to one personal computer at a central location for review by a systems administrator. This reduces the length of wiring between the elastomeric flexible element and the LCR meter, so that the parasitic capacitance of the wiring does not have a significant effect on the measurements, and the wiring does not pick up significant electrical noise or interference. At present low-cost microcontrollers are commercially available that have on-chip analog-to-digital and digital-to-analog converters, so that it is economical to program such a microcontroller to function as an LCR meter. In contrast to a commercial LCR meter designed for a wide range of measurements, the microcontroller-based LCR meter need operate at only one frequency best suited for the nominal capacitance of its companion composite elastomeric flexible joint. Therefore the microcontroller-based LCR meter may have a simplified construction for cost savings, power savings, and increased reliability.

In the example of FIG. 11, the microcontroller 140 has one digital-to-analog converter 141 and a pair of matched analog-to-digital converters 142 and 143. The microcontroller 140 also has a microprocessor 144, a read-only memory 145, a random-access memory 146, an interrupt timer 147, and a serial interface 148. The read-only memory 145 stores a program 149 of computer instructions executed by the microprocessor 144, and a sine/cosine table 150. For example, the microcontroller 140 is a Freescale Semiconductor part No. MC56F847 digital signal controller.

The serial interface 148 receives data from the personal computer on a first twisted pair 151, and transmits data to the personal computer on a second twisted pair 152. For example, data is transmitted and received in accordance with the RS232 standard.

In general, a conventional LCR meter functions by exciting both a reference impedance ($Z_{REF}$) and the impedance to be measured ($Z_{CEFE}$) with an AC reference signal at a selected frequency so that the same current flows through both the reference impedance and the impedance to be measured. This results in a corresponding AC voltage $V_{REF}$ across the reference impedance, and a corresponding AC voltage $V_{CEFE}$ across the impedance to be measured. The LCR meter converts each AC voltage into a phasor voltage that is a complex number having a real value component and an imaginary value component. The real value is the correlation of the AC voltage with a cosine reference signal used to generate the exciting AC signal. The imaginary value is the correlation of the AC voltage with a sine reference signal; in other words, the sine reference signal lags the cosine reference signal by 90 degrees. The LCR meter uses complex number arithmetic to compute the value of the impedance to be measured from the two phasor voltages and the known value of the reference impedance as $Z_{CEFE}=Z_{REF}V_{CEFE}/V_{REF}$.

In the example of FIG. 11, oversampling techniques of digital signal processing are used to generate the exciting AC voltage and compute the correlations. For example, the exciting AC voltage is generated at 1 KHz by oversampling at 64 KHz. The interrupt timer 147 is programmed to periodically interrupt the microprocessor 144 at a rate of 64 KHz. The interrupt routine increments a pointer used to address the sine/cosine table 150, and writes a cosine value from the table to the digital-to-analog converter 141. The interrupt routine then reads a voltage value from the first analog-to-digital converter 142, and multiplies it by the cosine value, and accumulates the product for computation of the correlation of the voltage with the cosine reference. The interrupt routine also multiplies the voltage value from the first analog-to-digital converter 142 by a corresponding sine value read from the sine/cosine table 150 using the same pointer value, and accumulates the product for computation of the correlation of the voltage with the sine reference. The interrupt routine reads a voltage from the second analog-to-digital converter 143 and performs similar operations upon this voltage to accumulate products for computation of the correlation of this voltage with the cosine reference and for computation of the correlation of this voltage with the sine reference.

The microprocessor 144 also has a lower priority interrupt routine that operates at a lower rate, such as a 1 Hertz rate, to calculate the measured impedance values from the complex numbers represented by the accumulated products. The measured impedance values are buffered in the random access memory 146, and transmitted to the personal computer via the serial interface 148 in response to a request from the personal computer. For example, the personal computer includes an address of the microcontroller 140 in the request, and the microcontroller 140 does not respond to the request unless the request includes the address of the microcontroller 140. In this way, multiple microcontrollers can be connected in parallel to the twisted pairs 151, 152 in order to share a single serial interface of the personal computer.

In the example of FIG. 11, the reference impedance $Z_{REF}$ 153 is selected to have a value that is the nominal impedance of the companion composite elastomeric flexible joint under a nominal load. For example, the reference impedance $Z_{REF}$ 153 is the parallel combination of one or more metal film resistors and one or more silver mica capacitors. The reference impedance $Z_{REF}$ 153 and the composite elastomeric flexible element $Z_{CEFE}$ 154 are excited by a driver 155 and a center-tapped transformer 156 to provide a bridge circuit that is balanced when the composite elastomeric flexible element $Z_{CEFE}$ 154 has the nominal impedance of the reference impedance $Z_{REF}$ 153. Therefore, the analog-to-digital converter 142 is sampling a relatively small signal when the composite elastomeric flexible element $Z_{CEFE}$ 154 is carrying a nominal load and there has been no degradation of the elastomer, and consequently the analog-to-digital converter 142 circuit is capable of resolving a wider range of deviation from the nominal condition. Due to the bridge circuit, the analog-to-digital converter 142 converts the differential value $V_D=V_{CEFE}-V_{REF}$ so that microprocessor 144 computes value of the impedance to be measured as $Z_{CEFE}=Z_{REF}+Z_{REF}V_D/V_{REF}$.

Figure 12:
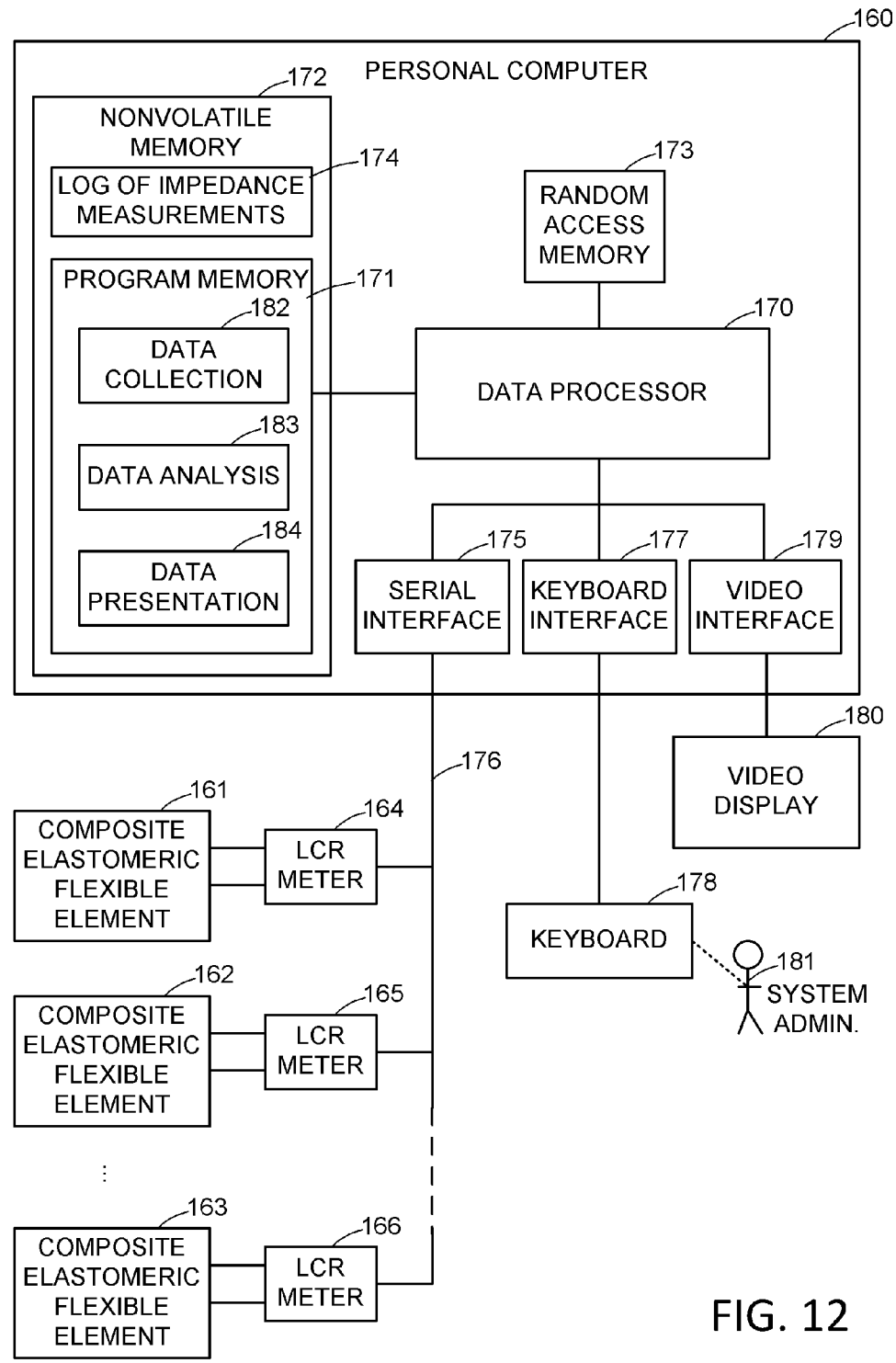
FIG. 12 is a block diagram of a system for monitoring the health of the multiple composite elastomeric flexible elements in the floating offshore drilling and production facility of FIG. 1.

FIG. 12 shows further details of a personal computer 160 programmed for collecting impedance measurements from multiple composite elastomeric flexible elements 161, 162, 163, each having a respective companion LCR meter 164, 165, 166. The computer 160 includes a data processor 170 for executing computer program instructions stored in a program memory 171. The program memory 171, for example, is a portion of nonvolatile memory 172, such as a hard disk drive or flash memory. The computer 160 also has random access memory 173 for caching instructions to be executed, for storing results of calculations, and for buffering data received from the LCR meters 164, 165, 166. The data received from the LCR meters is read from the random access memory 173 and written to a log of impedance measurements 174 in the non-volatile memory 172. The personal computer 160 has a serial interface 175 coupled via a serial data bus 176 to the LCR meters 164, 165, 166 for collection of the impedance measurements. The personal computer 160 also has a keyboard interface 177 linked to a keyboard 178, and a video interface 179 linked to a video display 180. A systems administrator 181 operates the personal computer 160 via the keyboard 178 or other input/output devices, such as a mouse, or a touch screen on the video display 180.

The program memory 171 stores data collection routines 182, data analysis routines 183, and data presentation routines 184. The data collection routines 182 periodically address the LCR meters 164, 165, 166 to collect impedance measurements, which are stored in the log 174. The data analysis routines 183 analyze the impedance measurements to assess the health of the elastomer in the composite elastomeric flexible elements 161, 162, 163, and to detect degradation of the elastomer and to alert the system administrator 181 of abnormal degradation and diagnose and report possible causes of the abnormal degradation. The data presentation routines 184 present the log of impedance measurements 174 to the system administrator 181 as a graph of capacitance and resistance measurements as a function of time, in a form similar to that depicted in FIG. 5.

In general, the data analysis routines 183 take advantage of the property that both capacitance and axial stiffness of an elastomer layer are a function of the compression load. The elastomeric pads are subject to mechanical compression as well as rotation or shear during operation. The elastomeric pads deform and develop mechanical damage under the action of sustained and cyclic compression or rotation. In general, the time that it takes an elastomeric pad to develop a prescribed amount of damage under load is correlated with the evolution of the axial stiffness of the pad; that is, with the ratio of the axial load to the axial deflection of the pad under load. Therefore, under a constant load, during the early and middle lifetime of the pad, the thickness of the pad will slowly decrease, causing a corresponding increase in capacitance of the elastomer layer because the capacitance of a capacitor changes inversely in proportion to the distance between the conductive plates of the capacitor. In the usual case, the remaining time for an elastomeric pad to develop a prescribed amount of damage is estimated through correlation of the change in capacitance with the loading for the particular pad and the known history of the time to damage under loading in the usual case. Moreover, at the end of life of the pad, or in response to an abnormally high load, substantial damage of the elastomer may occur as voids form in the elastomer. This kind of damage is indicated by a decrease in capacitance without a corresponding decrease in load. In either the case of a gradual increase in capacitance or a sudden decrease in capacitance, a graphical presentation on the video display 180 of the capacitance measurements over time from the log 174 provides a report to the systems administrator 181 of an indication of health of each composite elastomeric flexible element 161, 162, 163 in the facility.

The capacitance measurements can be adjusted based on displacement or load measurements so that the report to the systems administrator 181 conveys the changes in capacitance due to the aging or degradation of the elastomer rather than changes in capacitance due to changes in displacement or load. Because the capacitance of a capacitor changes inversely in proportion to the distance between the conductive plates of the capacitor, a relative change in capacitance can be adjusted based on the displacement or load measurements by subtracting out or factoring out the relative change in thickness of the elastomer layer. If the composite elastomeric flexible element does not have an associated displacement sensor but has an associated load sensor, then the relative change in the thickness of the elastomer layer can be estimated as the change in thickness due to the change in load in accordance with a nominal spring constant (K) of the elastomer layer, divided by a nominal thickness of the elastomer layer.

Changes in capacitance due to degradation of the elastomer can also be correlated with changes in resistance of the elastomer layers and transient load events to assess the nature and severity of degradation of the elastomer. Therefore the graphical presentation on the video display 180 includes the resistance measurements as well as the capacitance measurement from the log 174, and also any corresponding displacement or load measurements, as a function of time on the same graph, in a fashion similar to FIG. 5. By comparing the real-time data to baseline measurements and historical trends, the data analysis routines 183 can detect and diagnose potential problems, and the data presentation routines 184 can alert the system administrator 181 to these potential problems.

Figure 13:
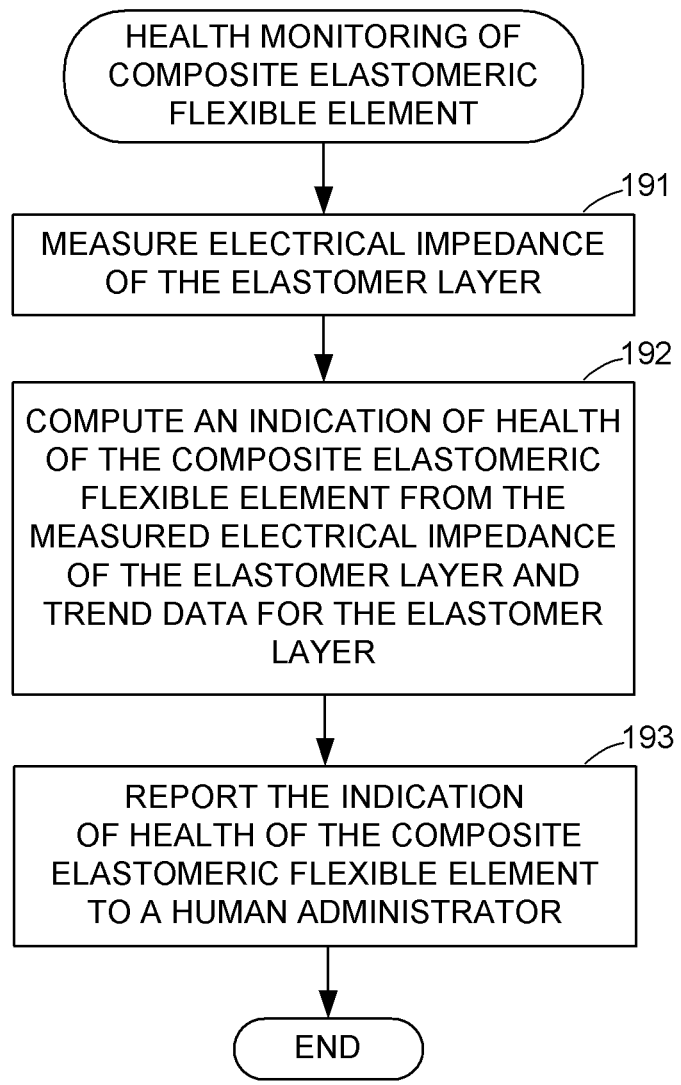
FIG. 13 is a flowchart of a basic method of health monitoring used in the system of FIG. 12 for integrity management of the multiple composite elastomeric flexible elements.

FIG. 13 shows a basic method of health monitoring used in the system of FIG. 12 for integrity management of a composite elastomeric flexible element. In a first step 191, electrical impedance of the elastomer layer is measured. This can be done by measuring capacitance of the elastomer layer. For example, the capacitance of the elastomer layer is measured by an LCR meter, as described above with reference to FIG. 4 and FIGS. 9-11. The capacitance can be measured in various other ways that compare the capacitance of the elastomer layer to a reference impedance. For example, the capacitance of the elastomer layer can be compared to a reference capacitance of a capacitor in a bridge circuit, by measuring AC voltages in bridge circuit. In another example, the capacitance of the elastomer layer can be compared to a reference resistance in an oscillator or timer circuit, for example in an oscillator or timer circuit using a timer integrated circuit such as part no. 555. In yet another example, the capacitance of the elastomer layer can be compared to a reference inductance (L) in an oscillator circuit including the capacitance of the elastomer layer ($C_e$) by measuring a frequency of oscillation $\omega=1/(LC_e)^{1/2}$.

Electrical impedance of the elastomer layer also can be measured by measuring transmission or reflection of an electromagnetic signal through the elastomer layer. For example, the electromagnetic signal can be a microwave signal propagating through the elastomer layer as an electromagnetic wave in a wave guide, or a signal propagating over a transmission line that is embedded in the elastomer layer. The permittivity ($\epsilon$) of the elastomer layer affects the velocity (v) of propagation according to $v=1/(\mu\epsilon)^{1/2}$, where $\mu$ is the magnetic permeability. The time for transmission of the signal over a known length of the transmission line can be measured, and the permittivity can be calculated from the transmission time. Alternatively, permittivity of the elastomer can be calculated from a measurement of phase or amplitude of standing waves that arise from reflection of signals propagating over the transmission line, for example as measured by a voltage standing wave ratio (VSWR) meter.

Electrical impedance of the elastomer layer can be measured by measuring resistance of the elastomer layer. For example, the resistance of the elastomer layer is measured by an LCR meter, as described above with reference to FIG. 4 and FIGS. 9-11. The resistance can be measured in various other ways that compare the resistance of the elastomer layer to a reference impedance. The resistance can be measured by using a DC ohm meter, which measures the DC current resulting when a DC voltage is applied to the elastomer layer. The resistance can be measured in an AC bridge circuit that compares the resistance to a reference impedance, which could be a capacitor, resistor, or inductor, or a combination of these components. The resistance can also be measured by measuring attenuation of an electromagnetic signal propagating through the elastomer layer. For example, the electromagnetic signal can be a microwave signal propagating through the elastomer layer as an electromagnetic wave in a wave guide, or a signal propagating over a transmission line that is embedded in the elastomer layer.

In step 192, an indication of health of the composite elastomeric flexible element is computed from the measured electrical impedance of the elastomer layer and trend data for the elastomer layer. For example, the indication of health is an amount of relative change in the measured electrical impedance of the elastomer layer. The relative change is the difference from a nominal value, divided by the nominal value. For example, the nominal value is the initial value of the measured electrical impedance of the elastomer layer under an initial load when the composite elastomeric flexible element was installed and put under the initial load. The relative change can be adjusted to discount changes due a change in the thickness of the elastomer layer, or due to load applied to the elastomer layer. If degradation of the elastomer is indicated, the degradation of the elastomer may be correlated with abnormal loading of the elastomer layer. The indication of health of the composite elastomeric flexible element can also be a graph of impedance such as capacitance or resistance as a function of time, or a graph correlating changes in impedance with changes in displacement or load.

In step 192, the indication of health of the composite elastomeric flexible element could be an estimate of the remaining time until the composite elastomeric flexible element would reach a pre-established state of damage under load. For example, if the historical trend indicates that the capacitance of a particular elastomer layer has gradually increased by ten percent over five years under a nominal load since installation, and the capacitance of an average elastomer layer of the same geometry and composition increases by ten percent over ten years under this nominal load since installation and reaches a state of beginning of extrusion at thirty years since installation, then the estimate of the remaining time for the particular elastomer layer is calculated as ten years until extrusion would begin. This example assumes that the increased rate of aging of the particular elastomer layer over the beginning of its life, as indicated by its relative decrease in capacitance in comparison to the relative decrease in capacitance for an average elastomer layer, will continue at the same increased rate of aging until the end of its life.

In step 193, the indication of health of the composite elastomeric flexible element is reported to a human administrator. If degradation of the elastomer is indicated, then the human administrator may take appropriate action, such as reducing the load on the composite elastomeric flexible element, or scheduling replacement of the composite elastomeric flexible element.

Figure 14:
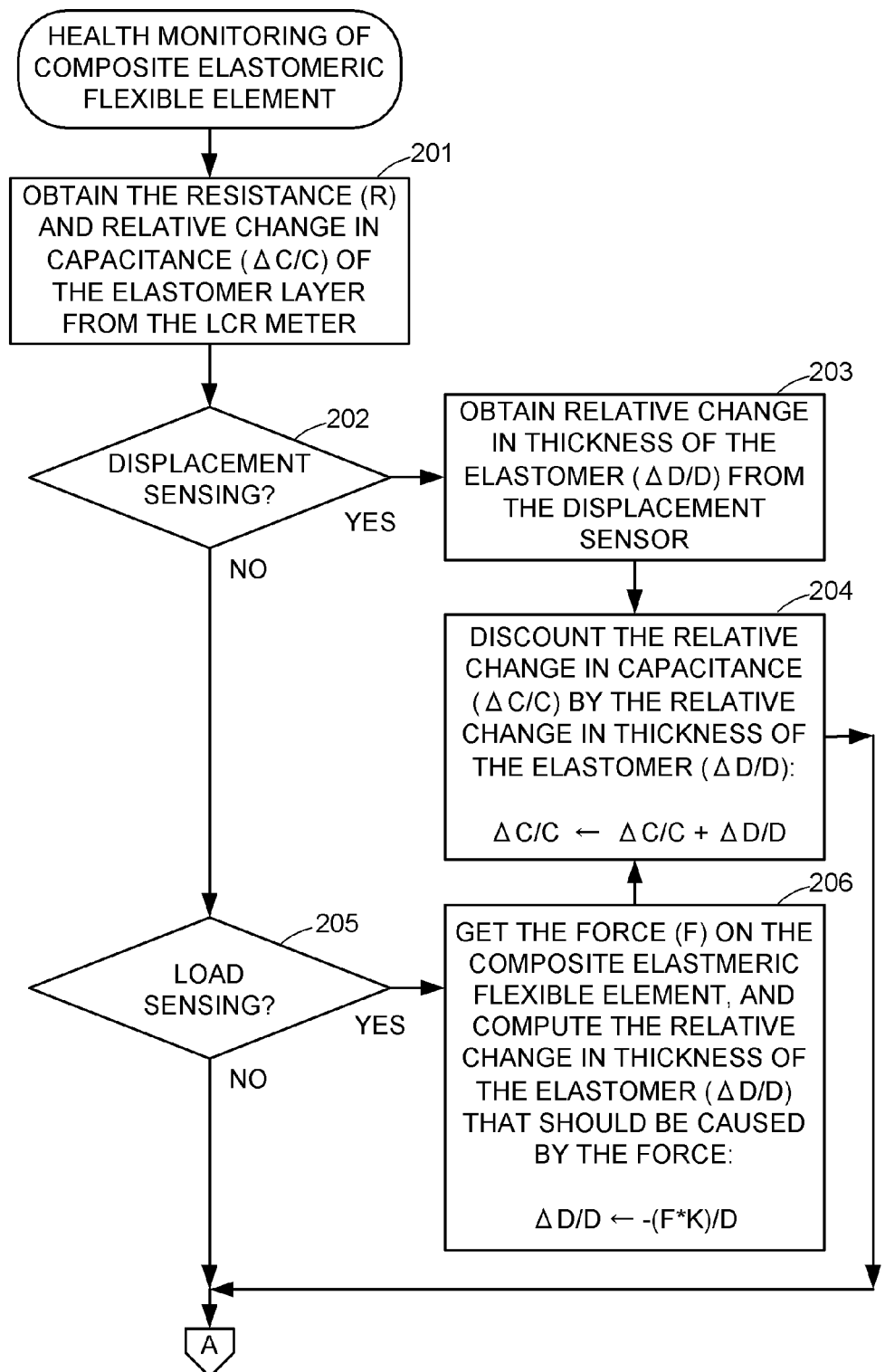
FIGS. 14, 15, and 16 together comprise a flowchart of a computer program routine in the personal computer of FIG. 12 to perform health monitoring of the multiple composite elastomeric flexible elements.
Figure 15:
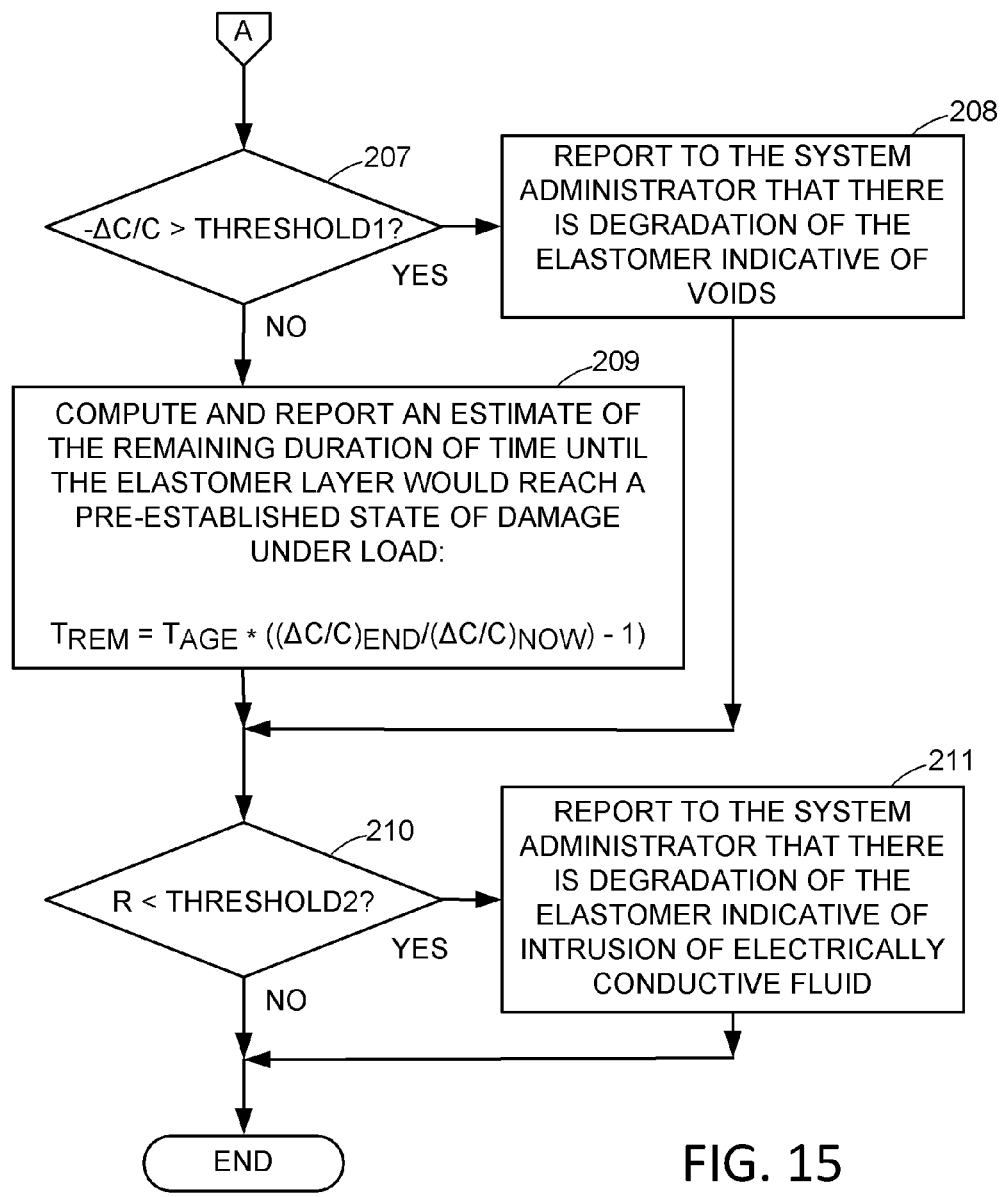
Figure 16:
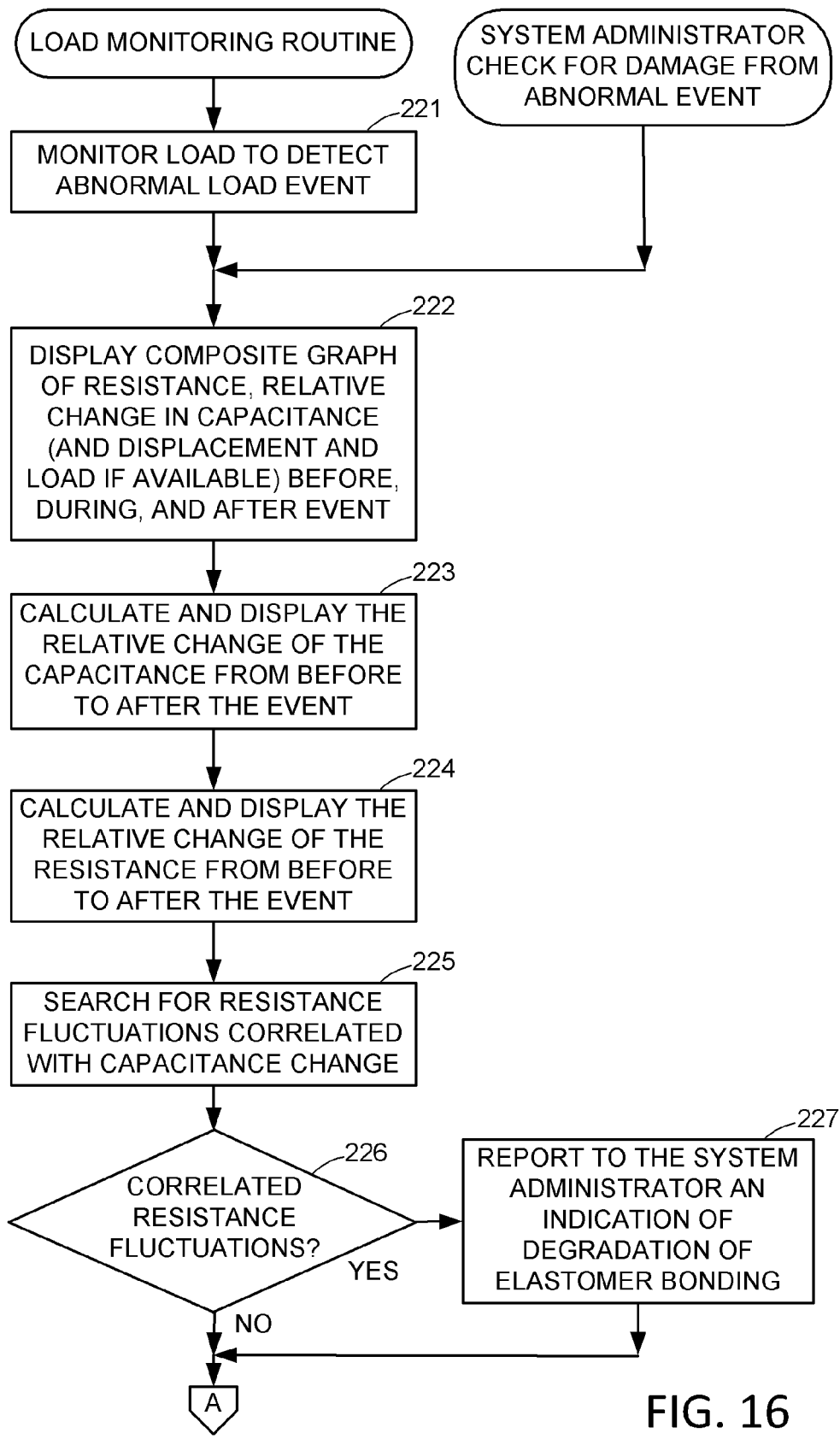

FIGS. 14, 15, and 16 together comprise a flowchart of the data analysis routine (183 in FIG. 12) in the personal computer (160 in FIG. 12) to perform health monitoring of the composite elastomeric flexible elements. In a first step 201, the data processor (170 in FIG. 12) obtains the resistance (R) and relative change in capacitance ($\Delta C/C$) of the elastomer layer from the LCR meter. For example, these values are read from the log (174 in FIG. 12) once the data collection routine (182 in FIG. 12) has collected them from the LCR meters (164, 165, 166 in FIG. 12) and has written them to the log (174 in FIG. 12).

Next, in step 202, execution branches to step 203 if there is displacement sensing indicative of the thickness of the elastomer layers. If so, then execution branches to step 203. In step 204, the relative change in the thickness of the elastomer ($\Delta D/D$) is obtained from a displacement sensor. Then, in step 205, the relative change in capacitance ($\Delta C/C$) is discounted by the relative change in thickness of the elastomer ($\Delta D/D$). For example, the data processor discounts the relative change in capacitance according to $\Delta C/C \leftarrow \Delta C/C + \Delta D/D$. Execution continues from step 204 to step 207 of FIG. 15.

In step 202, if there is not displacement sensing, then execution continues to step 205. In step 205, if there is sensing of load upon the composite elastomeric flexible element, then execution branches to step 206. In step 206, the data processor gets the force (F) on the composite elastomeric flexible element from a load sensor, and computes the relative change in thickness of the elastomer ($\Delta D/D$) that should be caused by the force. For example, the data processor computes the relative change in thickness of the elastomer from the compressive force (F) and a nominal spring constant (K) of the composite elastomeric flexible element according to $\Delta D/D \leftarrow -(F*K)/D$. Execution continues from step 206 to step 204, so that the computed relative change in thickness of the elastomer is used in step 204 to discount the relative change in capacitance.

In step 205, if there is not load sensing, then execution continues to step 207 of FIG. 15. In step 207, if the relative change in capacitance ($\Delta C/C$) is greater than a first threshold, then execution branches to step 208 to report to the system administrator that there is degradation of the elastomer indicative of voids. Execution continues from step 208 to step 210. In step 207, if the relative change in capacitance ($\Delta C/C$) is not greater than the first threshold, then execution continues to step 209.

In step 209, the data processor computes and reports to the system administrator an estimate of the remaining duration of time until the elastomer layer would reach a pre-established state of damage under load. For example, if it is assumed that the relative change in capacitance ($\Delta C/C$) since the installation and loading of the elastomer layer is a linear function of time up to the time of the pre-established state of damage, then in accordance with this linear model, the estimate of the remaining time ($T_{REM}$) is calculated as the present age ($T_{AGE}$) of the elastomer layer (i.e., the duration of time that the elastomer layer has been under load since installation) multiplied by the difference between a ratio of relative capacitance and one. The ratio of relative capacitance is the ratio of the expected relative change in capacitance at the time of the pre-established state of damage under load (($\Delta C/C)_{END}$) and the current relative change in capacitance (($\Delta C/C)_{NOW}$) since the time of installation. For example, if the elastomer layer has been in service for ten years and the current relative change in capacitance $((\Delta C/C)_{NOW})$ is one-half of the expected relative change in capacitance $((\Delta C/C)_{END})$ at the end of its useful life, then the estimated remaining lifetime $(T_{REM})$ is ten years. Once the current relative change in capacitance $((\Delta C/C)_{NOW})$ becomes equal to the expected relative change in capacitance at the end of its useful life, the estimated remaining lifetime is zero. This linear model could be modified to take into consideration variations in loading or temperature over the lifetime of the elastomer layer, so that the expected rate of aging of the elastomer layer would increase with increased loading and increased temperature. This linear model could also be modified to take into consideration the average measured relative change in capacitance as a function of time since installation for a population of elastomer layers having a similar composition, geometry, loading, and temperature once a historical database of measurement logs becomes available. After step 209, execution continues to step 210.

In step 210, if the resistance (R) is less than a second threshold, then execution branches to step 211 to report to the system administrator that there is degradation of the elastomer indicative of intrusion of electrically conductive fluid. After step 211, the routine is finished. In step 210, if the resistance is not less than the threshold, then the routine is also finished.

FIG. 16 shows a routine for responding to an abnormal event such as an abnormal load event. An abnormal load event is detected in step 221 by continuously monitoring the load upon the composite elastomeric flexible element, and detecting if a substantial transient load occurs. Execution continues from step 221 to step 222. Step 222 is also an entry point reached at the request of the system administrator, when the system administrator checks for damage from an abnormal event.

In step 222, the data processor displays a composite graph of resistance and relative change in capacitance, before, during, and after the event. If there is sensing of displacement of the composite elastomeric flexible joint, then the composite graph also includes the displacement. If there is sensing of load upon the composite elastomeric flexible element, then the composite graph also includes the load. In step 223, the data processor calculates and displays the relative change in capacitance from before to after the event, in order to indicate the change caused by the event. In step 224, the data processor calculates and displays the relative change in resistance from before to after the event, in order to indicate the change caused by the event. In step 225, the data processor searches for resistance fluctuations correlated with capacitance change. In step 226, if there are such correlated resistance fluctuations, then execution branches to step 227. In step 227, the data processor reports an indication of degradation of elastomer bonding to the systems administrator. After step 222, execution continues to step 207 of FIG. 15. Execution also continues to step 207 if no correlated resistance fluctuations are found in step 226.

In view of the above, there has been described a method and system for monitoring health of a composite elastomeric flexible element having an elastomer layer between rigid members. The health of a composite elastomeric flexible element is monitored by measuring electrical impedance of the elastomer layer, computing an indication of health of the composite elastomeric flexible element from the measured electrical impedance of the elastomer layer and trend data for the elastomer layer, and reporting the indication of health to a human administrator. Measurement of the electrical impedance of the elastomer layer may detect degradation before the elastomer layer fails to support a compressive load, although the degradation may significantly impair the ability of the elastomer to resist shear deformation and dampen loads and provide a fluid seal in a flexible pipe joint. The system administrator may respond to an indication of poor health of the composite elastomeric flexible element by reducing the load on the composite elastomeric flexible element, or scheduling replacement of the composite elastomeric flexible element.

What is claimed is:

1. A method of monitoring health of a composite elastomeric flexible element having an elastomer layer between rigid members, said method comprising:
   measuring electrical impedance of the elastomer layer;
   computing an indication of health of the composite elastomeric flexible element from the measured electrical impedance of the elastomer layer and trend data for the elastomer layer;
   measuring load upon the elastomer layer, and the computation of the indication of health of the composite elastomeric flexible element from the measured electrical impedance and trend data of the elastomer layer is responsive to the measured load upon the elastomer layer in order to discount a change in the measured electrical impedance of the elastomer layer due to a change in the measured load upon elastomer layer; and
   reporting the indication of health of the composite elastomeric flexible element to a human administrator.

2. The method as claimed in claim 1, which includes measuring load upon the composite elastomeric flexible element in order to detect a transient load capable of causing degradation of the elastomer layer, and in response to the detection of the transient load upon the composite elastomeric flexible element, computing an assessment of a change in health of the composite elastomeric flexible element due to the transient load upon the composite elastomeric flexible element from the indication of health of the composite elastomeric flexible element, and reporting to the human administrator the occurrence of the transient load and the assessment of the change in health of the composite elastomeric flexible element due to the transient load upon the composite elastomeric flexible element.

3. The method as claimed in claim 1, wherein the rigid members are electrically conductive, and the electrical impedance of the elastomer layer is measured by measuring capacitance of a capacitor comprised of the rigid members and the elastomer layer.

4. The method as claimed in claim 1, wherein the indication of health of the composite elastomeric flexible element is computed from the measured electrical impedance of the elastomer layer and trend data for the elastomer layer by detecting a relative change in electrical permittivity of the elastomer layer indicating formation of voids or the rupture of polymer chains in the elastomer layer.

5. The method as claimed in claim 1, which further includes measuring thickness of the elastomer layer, and the computation of the indication of health of the composite elastomeric flexible element from the measured electrical impedance and trend data of the elastomer layer is responsive to the measured thickness of the elastomer layer in order to discount a change in the measured electrical impedance of the elastomer layer due to a change in the measured thickness of the elastomer layer.

6. The method as claimed in claim 1, wherein the computation of the indication of health of the composite elastomeric flexible element from the measured electrical impedance and trend data of the elastomer layer includes computing an estimate of a remaining duration of time until the elastomer layer would reach a pre-established state of damage under load.

7. The method as claimed in claim 1, wherein the rigid members are electrically conductive, and the electrical impedance of the elastomer layer is measured by measuring electrical resistance between the rigid members.

8. The method as claimed in claim 1, wherein the computation of the indication of health of the composite elastomeric flexible element from the measured electrical impedance and trend data of the elastomer layer includes detecting a fluctuation in electrical resistance between the rigid members indicating slippage between the elastomer layer and at least one of the rigid members.

9. The method as claimed in claim 1, wherein the computation of the indication of health of the composite elastomeric flexible element from the measured electrical impedance and trend data of the elastomer layer includes detecting a decrease in electrical resistance between the rigid members indicating intrusion of electrically conductive fluid into the elastomer layer.

10. A system for monitoring health of a composite elastomeric flexible element having an elastomer layer between rigid members, said system comprising:
   a circuit for measuring electrical impedance of the elastomer layer;
   a data processor coupled to the circuit for receiving a measurement of electrical impedance of the elastomer layer, and executing computer program instructions stored in memory to perform the steps of computing an indication of health of the composite elastomeric flexible element from the measured electrical impedance and trend data of the elastomer layer, and reporting the indication of health of the composite elastomeric flexible element to a human administrator; and
   a load sensor coupled to the data processor for measuring load upon the elastomer layer, and the computation of the indication of health of the composite elastomeric flexible element from the measured electrical impedance and trend data of the elastomer layer is responsive to the measured load upon the elastomer layer in order to discount a change in the measured electrical impedance of the elastomer layer due to a change in the measured load upon the elastomer layer.

11. The system as claimed in claim 10, wherein the computation of the indication of health of the composite elastomeric flexible element from the measured electrical impedance and trend data of the elastomer layer includes detecting a decrease in electrical resistance between the rigid members indicating intrusion of electrically conductive fluid into the elastomer layer.

12. The system as claimed in claim 10, wherein the rigid members are electrically conductive, and the circuit includes a capacitance and resistance meter coupled to the rigid members for measuring capacitance and resistance of the elastomer layer.

13. The system as claimed in claim 10, wherein the composite elastomeric flexible element includes a stack of multiple electrically conductive rigid members including neighboring pairs of rigid members, and a respective elastomer layer between each of the neighboring pairs of rigid members, and the circuit includes a multiplexer for providing an electrical connection to a selected one of the neighboring pairs of rigid members for measuring electrical impedance of the respective elastomer layer between the selected one of the neighboring pairs of rigid members.

14. The system as claimed in claim 10, which further includes a load sensor for measuring load upon the composite elastomeric flexible element, and the data processor is coupled to the load sensor to receive a measurement of the load upon the composite elastomeric flexible element, and the program instructions, when executed by the data processor, perform the steps of detecting a transient load capable of causing degradation of the elastomer layer, and in response to the detection of the transient load upon the composite elastomeric flexible element, computing an assessment of a change in health of the composite elastomeric flexible element due to the transient load upon the composite elastomeric flexible element from the indication of health of the composite elastomeric flexible element, and reporting to the human administrator the occurrence of the transient load and the assessment of the change in health of the composite elastomeric flexible element due to the transient load upon the composite elastomeric flexible element.

15. The system as claimed in claim 10, wherein the computer program instructions, when executed by the data processor, compute the indication of health of the composite elastomeric flexible element from the measured electrical impedance and trend data of the elastomer layer by detecting a relative change in electrical permittivity of the elastomer layer indicating formation of voids in the elastomer layer.

16. The system as claimed in claim 10, which further includes a position sensor coupled to the data processor for measuring thickness of the elastomer layer, and the computation of the indication of health of the composite elastomeric flexible element from the measured electrical impedance and trend data of the elastomer layer is responsive to the measured thickness of the elastomer layer in order to discount a change in the measured electrical impedance of the elastomer layer due to a change in the measured thickness of the elastomer layer.

17. The system as claimed in claim 10, wherein the computation of the indication of health of the composite elastomeric flexible element from the measured electrical impedance and trend data of the elastomer layer includes computing an estimate of a remaining duration of time until the elastomer layer would reach a pre-established state of damage under load.

18. The system as claimed in claim 10, wherein the computation of the indication of health of the composite elastomeric flexible element from the measured electrical impedance and trend data of the elastomer layer includes detecting a fluctuation in electrical resistance between the rigid members indicating slippage between the elastomer layer and at least one of the rigid members.

19. A system for monitoring health of a composite elastomeric flexible element having an elastomer layer between rigid members, said system comprising:
   a circuit for measuring electrical impedance of the elastomer layer;
   a load sensor for measuring load upon the composite elastomeric flexible element; and
   a data processor coupled to the circuit for receiving a measurement of electrical impedance of the elastomer layer and the load sensor to receive a measurement of the load upon the composite elastomeric flexible element, and executing computer program instructions stored in memory to perform the steps of computing an indication of health of the composite elastomeric flexible element from the measured electrical impedance and trend data of the elastomer layer, detecting a transient load capable of causing degradation of the elastomer layer, and in response to the detection of the transient load upon the composite elastomeric flexible element, computing an assessment of a change in health of the composite elastomeric flexible element due to the transient load upon the composite elastomeric flexible element from the indication of health of the composite elastomeric flexible element, and reporting the indication of health of the composite elastomeric flexible element and the occurrence of the transient load and the assessment of the change in health of the composite elastomeric flexible element due to the transient load upon the composite elastomeric flexible element to a human administrator.

20. A system for monitoring health of a composite elastomeric flexible element having an elastomer layer between rigid members, said system comprising:
   a circuit for measuring electrical impedance of the elastomer layer;
   a data processor coupled to the circuit for receiving a measurement of electrical impedance of the elastomer layer, and executing computer program instructions stored in memory to perform the steps of computing an indication of health of the composite elastomeric flexible element from the measured electrical impedance and trend data of the elastomer layer, and reporting the indication of health of the composite elastomeric flexible element to a human administrator; and
   a position sensor coupled to the data processor for measuring thickness of the elastomer layer, and the computation of the indication of health of the composite elastomeric flexible element from the measured electrical impedance and trend data of the elastomer layer is responsive to the measured thickness of the elastomer layer in order to discount a change in the measured electrical impedance of the elastomer layer due to a change in the measured thickness of the elastomer layer.

21. A method of monitoring health of a composite elastomeric flexible element having an elastomer layer between rigid members, said method comprising:
   measuring electrical impedance of the elastomer layer;
   computing an indication of health of the composite elastomeric flexible element from the measured electrical impedance of the elastomer layer and trend data for the elastomer layer;
   measuring load upon the composite elastomeric flexible element in order to detect a transient load capable of causing degradation of the elastomer layer, and in response to the detection of the transient load upon the composite elastomeric flexible element, computing an assessment of a change in health of the composite elastomeric flexible element due to the transient load upon the composite elastomeric flexible element from the indication of health of the composite elastomeric flexible element; and
   reporting the indication of health of the composite elastomeric flexible element and the occurrence of the transient load and the assessment of the change in health of the composite elastomeric flexible element due to the transient load upon the composite elastomeric flexible element to a human administrator.

22. A method of monitoring health of a composite elastomeric flexible element having an elastomer layer between rigid members, said method comprising:
   measuring electrical impedance of the elastomer layer;
   computing an indication of health of the composite elastomeric flexible element from the measured electrical impedance of the elastomer layer and trend data for the elastomer layer
   measuring thickness of the elastomer layer, and the computation of the indication of health of the composite elastomeric flexible element from the measured electrical impedance and trend data of the elastomer layer is responsive to the measured thickness of the elastomer layer in order to discount a change in the measured electrical impedance of the elastomer layer due to a change in the measured thickness of the elastomer layer; and
   reporting the indication of health of the composite elastomeric flexible element to a human administrator.

* * * * *